United States Patent
Logroscino et al.

[11] Patent Number: 5,542,946
[45] Date of Patent: Aug. 6, 1996

[54] HOOK FOR AN OCCIPITO-CERVICAL ROD OR PLATE OF AN OCCIPITO-CERVICAL OSTEOSYNTHESIS INSTRUMENTATION

[75] Inventors: Carlo Logroscino, Rome, Italy; Michel Goube, Hardelot, France

[73] Assignee: Sofamor S.N.C., Rang Du Fliers, France

[21] Appl. No.: 250,580

[22] Filed: May 27, 1994

[51] Int. Cl.⁶ .................................................. A61B 17/70
[52] U.S. Cl. .................................................. 606/61; 606/72
[58] Field of Search ........................ 606/61, 69, 70, 606/71, 72, 73, 60, 54, 59, 101

[56] References Cited

U.S. PATENT DOCUMENTS

| | | | |
|---|---|---|---|
| 4,047,523 | 9/1977 | Hall | 606/61 X |
| 4,815,453 | 3/1989 | Cotrel | 606/61 X |
| 5,181,917 | 1/1993 | Rogozinski | 606/61 X |
| 5,201,734 | 4/1993 | Cozad et al. | 606/62 |
| 5,257,993 | 11/1993 | Asher et al. | 606/61 |
| 5,263,954 | 11/1993 | Schlapfer et al. | 606/61 |
| 5,360,429 | 11/1994 | Jeanson et al. | 606/61 |
| 5,380,325 | 1/1995 | Lahille et al. | 606/61 |

FOREIGN PATENT DOCUMENTS

| | | | |
|---|---|---|---|
| 2649042 | 9/1978 | Germany | 606/61 |
| 1074514 | 2/1984 | U.S.S.R. | 606/61 |
| 1517954 | 10/1989 | U.S.S.R. | 606/61 |

*Primary Examiner*—Guy Tucker
*Attorney, Agent, or Firm*—Woodard, Emhardt, Naughton, Moriarty & McNett

[57] ABSTRACT

The hook (32) comprises a body (33) and a laminar portion (37) which is suitably profiled and adapted to penetrate a foramen opening at the base of the occiput against which it bears. The body is arranged to receive an osteosynthesis rod or plate and has a plane of symmetry (P). The laminar portion (37) has a curvature adapted to the thickness of the occipito-cervical shell and is inclined relative to one side or the other of the plane of symmetry (P) so as to be adaptable to the anatomy of the edge of the occiput in the region of the foramen. This inclination may be for example substantially 45°. This asymmetry of the laminar portion (37) relative to the body (33) of the hook (32) enables the surgeon to avoid having to previously remove a piece of the edge of the occiput of the patient and consequently damage the occiput.

4 Claims, 3 Drawing Sheets

5,542,946

1

HOOK FOR AN OCCIPITO-CERVICAL ROD OR PLATE OF AN OCCIPITO-CERVICAL OSTEOSYNTHESIS INSTRUMENTATION

BACKGROUND OF THE INVENTION

The present invention relates to an occipito-cervical osteosynthes is instrumentation and a hook intended to be part of this instrumentation.

It is known that in orthopaedic surgery on the cervical spine, when an instrumentation is required to realize an occipito-cervical arthrodesis, the surgeon generally uses an instrumentation composed of plates and screws. There has thus been put on the market an assembly having the general shape of a horseshoe constituted by two rods in one piece with a curved connection plate, the rods being knurled and disposed in the cervical part while the curved plate is in the occipital part. The hooking to the cervical vertebrae is achieved by thoracic and pediatric laminar hooks while the connection of the plate to the occiput is achieved by a plurality of screws.

This device has a drawback in that it cannot be shaped sufficiently to the anatomical configuration of the patient, above all in the cervical part. Indeed, it is difficult to adapt the distance between the two rods in the cervical part while achieving a suitable bending of the curved connecting plate.

Further, in orthopaedic surgery of the cervical segment, pathologies are encountered concerning the upper cervical vertebrae Atlas (C1) and Axis (C2). Among these there are essentially found degenerative pathology (cerviarthrosis) and tumoral traumatic pathology. When an instrumentation is used in the rear approach, this instrumentation comprises either rods or plates, their common purpous being to isolate the pathological segment by connecting the occiput to the subjacent healthy vertebrae. Thus there are known various instrumentation rods, frames and plates, in particular the Cotrel Dubousset rod, the Privat plate, the Roy Camille plate, etc. The means for connecting these different plates to the bone (occiput or vertebrae) comprise the following elements:

a) articular screws (inserted in the articular massives) and occipital screws, b) occipital screws and laminar hooks bearing against the vertebrae, c) metal wires constituting a bone lacing.

It is also known from the French patent application 92 01 913 (2 687 561) to construct an occipito-cervical device in which the two cervical rods are extended by curved plates which are themselves connected at their ends by a transverse connection plate. The assembly is fixed to the occiput by means of screws extending through openings in the connection plate so that a certain adjustment to the desired conformation is possible.

However, here again, the possibilities of an anatomical adaptation are in fact limited, notwithstanding the fact that this device provides a possibility of adjustment relative to the preceding device.

In order to fasten the rods of these instrumentations to the base of the occiput, there are in particular used hooks constituted by a body and a laminar portion which is adapted to enter the foramen opening at the base of the occiput against which the hook therefore bears. Now, the anatomy of the edge of the foramen in the regions where the hooks must bear is such that, in practice, in order to be in a position to conciliate both a correct orientation of the rod which extends through the body of the hook and a suitable bearing of the laminar portion of the latter on the base of the occiput, it is necessary to remove a piece of the occiput and therefore to damage it.

SUMMARY OF THE INVENTION

An object of the present invention is to provide a hook adapted to eliminate this drawback.

The hook for an occipito-cervical rod or plate of an occipito-cervical osteosynthesis instrumentation, comprises a body and a suitably profiled laminar portion adapted to penetrate the foramen opening at the base of the occiput against which it bears, the body being arranged to receive an osteosynthesis rod or plate and having a median plane of symmetry.

According to the invention, the laminar portion is inclined relative to one side or the other of said plane of symmetry so as to be adapted to the anatomy of the edge of the occiput in the region of the foramen.

Under these conditions, the hook may be suitably oriented and its laminar portion may obtain a satisfactory support on the edge of the foramen without requiring the surgeon to previously remove a piece of the occiput, which is obviously preferable for the patient.

The inclination of the laminar portion relative to the plane of symmetry is advantageously and preferentially on the order of about 45°, but may deviate from this angle in either direction.

BRIEF DESCRIPTION OF THE DRAWINGS

The invention will now be described with reference to the accompanying drawings which illustrate two embodiments thereof as non-limitative examples.

DESCRIPTION OF PREFERRED EMBODIMENTS

Figure 1:
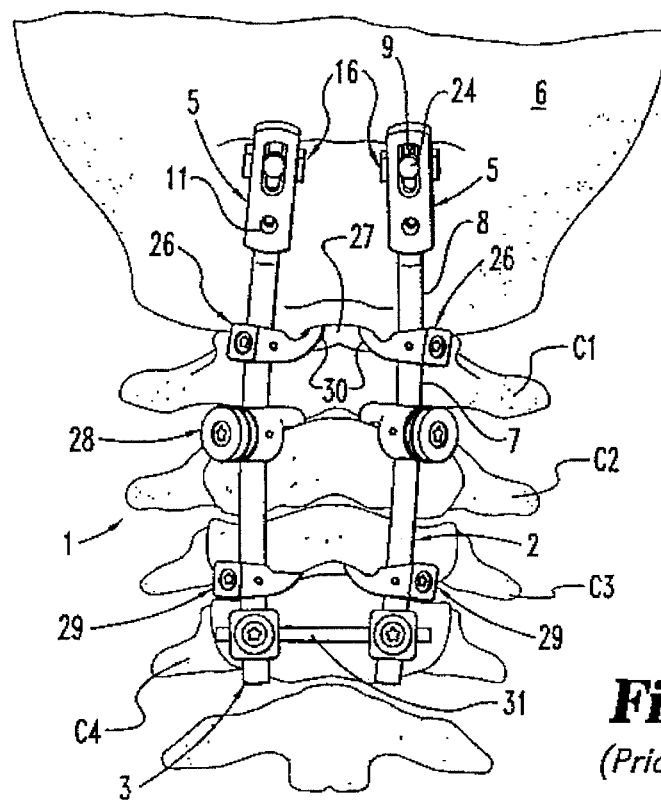
FIG. 1 is an elevational view to a small scale of an embodiment of the occipito-cervical instrumentation which may be equipped with hooks according to the invention, mounted on the first cervical vertebrae and on the occiput of a patient.
Figure 2:
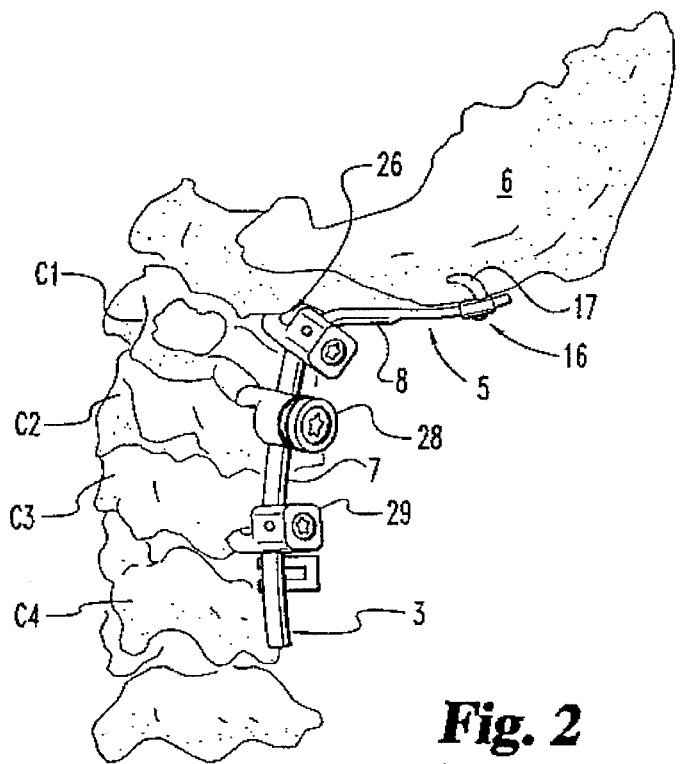
FIG. 2 is a side elevational view of the instrumentation of the cervical vertebrae and of the occiput of FIG. 1.
Figure 3:
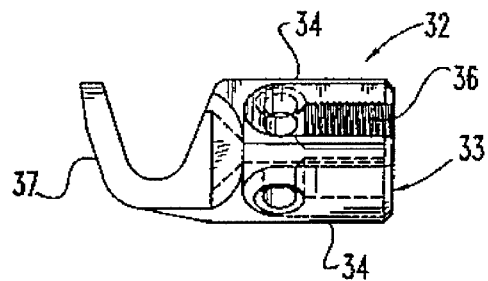
FIG. 3 is a side elevational view of a first embodiment of the occipital hook according to the invention.
Figure 4:
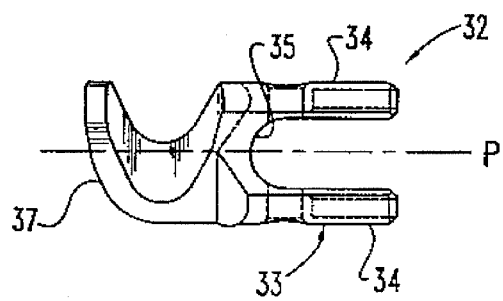
FIG. 4 is a side elevational view at a different angle of the hook of FIG. 3.

The complete instrumentation, placed on a cervical segment C1–C3 and on an occiput 6, shown in FIGS. 1 and 2, comprises two separate parts 1 and 2, respectively a left part and a right part, FIGS. 1 and 2 being views from the rear and side, respectively, of the patient. The parts 1 and 2 are identical as manufactured and each part comprises a cervical rod 3 having asperities and an elongate occipital plate 5. The latter is in one piece with the rod 3 and extends from the end of the latter in the direction toward the occiput 6 in the position of use.

Each rod 3 is constituted by two substantially rectilinear sections 7 and 8 which are pre-angulated so as to make therebetween an angle suitable for the anatomical curvature between the occiput 6 and the cervical vertebrae C1–C3. The occipital rod section 8 has a length much less than that of the cervical rod section 7, and is connected to the occipital plate 5 which is bent so as to enable it to conform to the curvature of the occipital shell. The rod section 8 connected to the plate 5 is adapted to extend, in the position of use, along the base of the occiput 6. Each part 1, 2 is so profiled as to be adapted to the anatomy of the occipito-cervical connection.

Provided in each elongate plate 5 are an oblong opening 9 and a circular opening 11, the latter being arranged in the vicinity of the junction between the plate 5 and the terminal portion 8 of the rod 3.

Screws 24 engaged in the oblong openings 9 fix respective occipital hooks 16 to the plates 5. Other hooks 26 of the closed body type have extending therethrough rod sections 7 just in front of the elbow formed by the latter with the terminal sections 8. Laminar or strip portions 30 extend in the conventional manner from the ends of the bodies of the hooks 26 and penetrate the foramen opening 27 at the base of the occiput 6 against which they bear. Screws fix the hooks 26 to the rods 3 in the known manner.

In the region of the cervical vertebrae C2–C3, the rods 3 are fixed by means of hooks 28 having an open body and a screw threaded inner plug (vertebra C2) and laminar hooks 29 having a closed body (vertebra C3). A transverse connection device 31 between the two rods 3 completes the instrumentation at the level of the vertebra C4.

The hook to which the present invention is particularly related is shown in detail in FIGS. 3 to 7.

In the first embodiment (FIGS. 3 and 4), the hook 32, adapted to replace the hook 26 for each rod, comprises a body 33 of open type, i.e. having a U shape delimited by two branches 34 whose inner surfaces form a channel having a semi-cylindrical bottom 35 adapted to serve as a seat for the rod 3.

Tapped portions 36 are arranged on the inner surfaces of the branches 34 which permit the screwing of a screw threaded plug (not shown) whereby the rod 3 can be clamped in the body 33, which has a plane of symmetry P with respect to which the two branches 34 are symmetrical.

The body 33 is extended by a curved laminar or strip portion 37 which is inclined relative to one side or the other of the plane of symmetry P so as to adapt itself to the anatomy of the edge of the occiput 6 in the region of the foramen 27. More precisely, the laminar portion 37 is itself symmetrical on each side of a median plane P1 angularly offset from the plane P by an angle A (FIG. 5) which advantageously may be on the order of about 45°.

Figure 5:
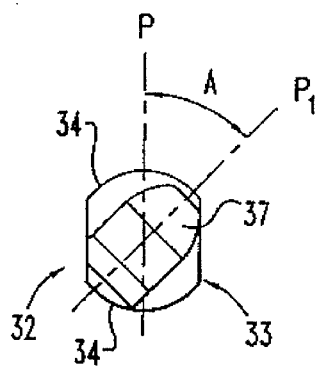
FIG. 5 is an end elevational view of the posterior end of the hook of FIGS. 3 and 4.
Figure 6:
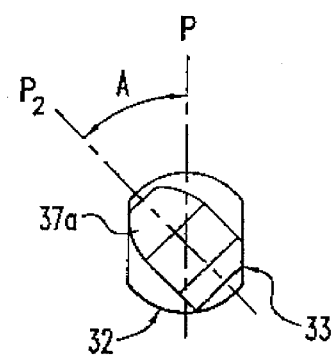
FIG. 6 is a view similar to FIG. 5 of an alternative embodiment of the hook.

This inclination may be either relative to the right side of the plane P (in viewing the hook 32 from its posterior end, i.e. from the body 33) as shown in the embodiment of FIG. 5, or relative to the left side of the plane P of the body 33 as illustrated in the alternative embodiment of FIG. 6.

Figure 7:
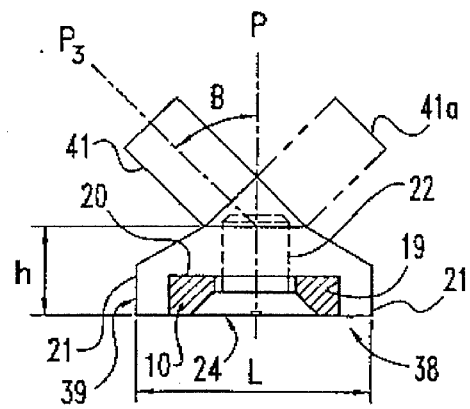
FIG. 7 is a side elevational view of a second embodiment of the hook according to the invention.
Figure 8:
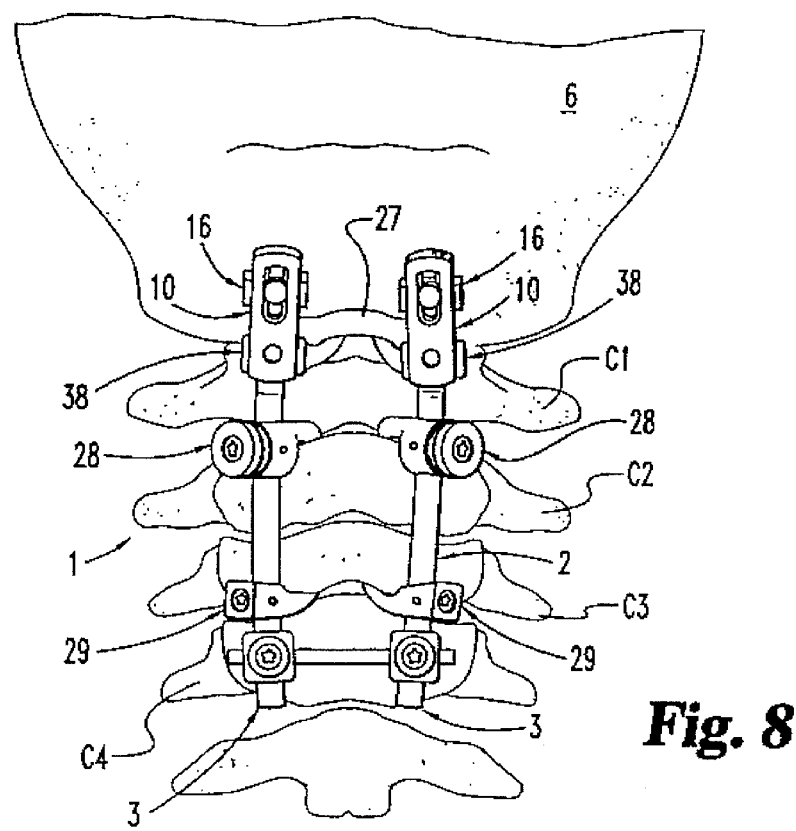
FIG. 8 is a view similar to FIG. 1 showing an alternative embodiment of the invention.
Figure 9:
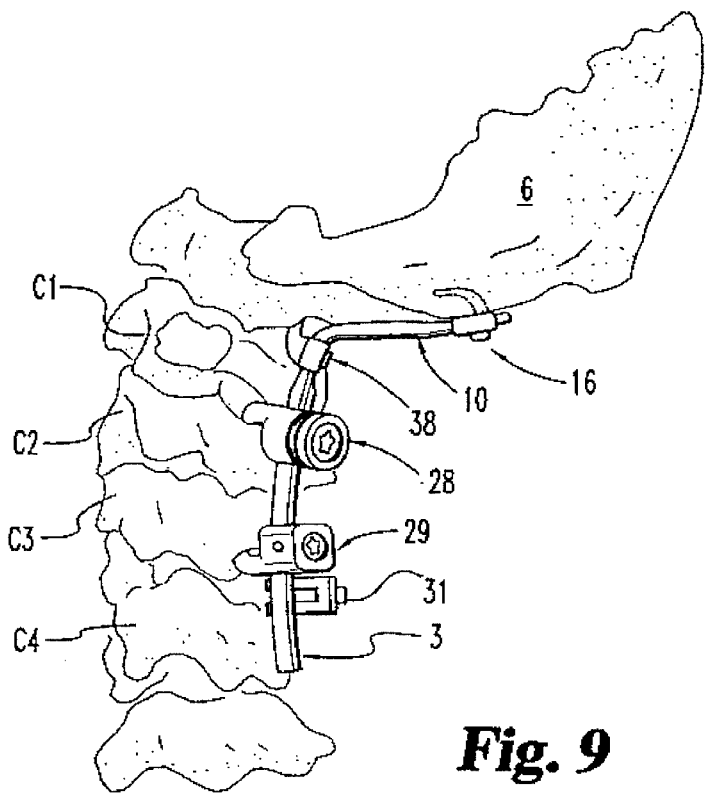
FIG. 9 is a side elevational view of view of the embodiment shown in FIG. 8.

In the second embodiment illustrated in FIGS. 7, 8 and 9, the hook 38 comprises a body 39 identical to the body of the prior hook. The height h of the body 39 is small with respect to its length L and there is provided in the body 38 a groove 19 for receiving and guiding the occipital plate 10, this groove being delimited by two parallel branches 21 of the body 39. These branches 21 form with the bottom 20 a U-sectioned channel which is shallow relative to its length. A tapped hole 22 is provided in the body 38, opens onto the bottom 20, and is in alignment with the oblong opening 9 when the plate 10 is inserted between the branches 19. The plate 10 is fixed to the hook 16 by the screw 24.

The plates 10 differ from the plates 5 in that they are extended downwardly from the occiput 6 to the level of the foramen opening 27. The plates 10 are bent and connected to the rods 3 just below the foramen opening 27.

The hook 39 differs from prior hooks in that its laminar portion 41 extends on each side of a median plane of symmetry P3 which is inclined relative to the plane of symmetry P of the body 39, either on the left side (as shown in full lines) or on the right side of the plane P as shown in dot-dash lines 41a.

The inclination B of the median plane P3 to the plane of symmetry P may vary more or less, as the inclination A of the preceding embodiment so as to be adapted to the particular anatomy in this region of the patient.

In all cases, the laminar portion 37 or 41 has a curvature adapted to the thickness of the occipito-cervical shell.

It must be understood that the embodiments illustrated in FIGS. 3 to 7 may be subjected to variations. Thus, it is in particular obvious that the hook may have a body different from those shown in FIGS. 3 to 7, for example the body may be closed in the same way as that of the hooks 26 of FIGS. 1 and 2.

What is claimed is:

1. Hook for an occipito-cervical rod or plate of an occipito-cervical osteosynthesis instrumentation, said hook comprising a generally U-shaped body with opposite side branches having a laminar portion defined by a strip suitably profiled and adapted to penetrate a foramen opening at the base of the occiput, said body being adapted to receive an osteosynthesis rod or plate and having a median plane of symmetry extending between said side branches, said strip being inclined relative to either side of said median plane of symmetry so as to adapt itself to the anatomy of the edge of the occiput in the region of the foramen.

2. Hook according to claim 1, wherein said strip has an inclination of substantially 45° relative to said median plane of symmetry.

3. Occipito-cervical osteosynthesis instrumentation comprising two separate similarly configured parts, namely a right part and a left part, each part including a cervical rod having asperities and an elongate occipital plate which is in one piece with said rod and extends said rod toward said occiput in the position of use, and adjustable means for anchoring said rod to the vertebrae C1– C3 and for anchoring said plate to said occiput, each of said parts being pre-angulated and so profiled as to be adapted to the anatomy of the occipito-cervical connection of the human spine, said adjustable means for anchoring said plate to said occiput comprising hooks adapted to penetrate the foramen openings at the base of said occiput against which they bear, each hook including a laminar portion and a generally U-shaped body with opposite side branches adapted to receive the rod or plate and having a median plane extending between said side branches and said laminar portion is inclined relative to either side of said plane of symmetry.

4. Instrumentation according to claim 3, wherein said laminar portion has an inclination of substantially 45° relative to said median plane of symmetry.

\* \* \* \* \*